(12) United States Patent
Stout et al.

(10) Patent No.: US 9,138,343 B2
(45) Date of Patent: Sep. 22, 2015

(54) TIP PROTECTOR SLEEVE

(75) Inventors: Christopher A. Stout, San Bruno, CA (US); Betsy Swann, Grass Valley, CA (US); Julian Cruzada, San Jose, CA (US); Chris Sepe, Campbell, CA (US)

(73) Assignee: Bayer Healthcare LLC, Whippany, NJ (US)

( * ) Notice: Subject to any disclaimer, the term of this patent is extended or adjusted under 35 U.S.C. 154(b) by 636 days.

(21) Appl. No.: 13/149,631

(22) Filed: May 31, 2011

(65) Prior Publication Data

US 2012/0310215 A1   Dec. 6, 2012

(51) Int. Cl.
| | |
|---|---|
| *A61M 5/178* | (2006.01) |
| *A61M 5/32* | (2006.01) |
| *A61F 6/06* | (2006.01) |
| *A61F 6/22* | (2006.01) |
| *A61B 17/42* | (2006.01) |
| *A61F 6/18* | (2006.01) |
| *A61B 17/12* | (2006.01) |
| *A61B 19/00* | (2006.01) |

(52) U.S. Cl.
CPC .............. *A61F 6/225* (2013.01); *A61B 17/42* (2013.01); *A61F 6/18* (2013.01); *A61B 2017/1205* (2013.01); *A61B 2019/304* (2013.01); *Y10T 29/49826* (2015.01)

(58) Field of Classification Search
CPC . A61M 25/09; A61M 25/0905; A61M 25/01; A61M 25/0074; A61M 25/0043; A61M 2025/0681; A61M 25/0133; A61F 6/225; A61F 6/18; A61B 17/42; A61B 2017/1205; A61B 2019/304; Y10T 29/49826
USPC ............. 604/528, 95.01, 263, 264, 158, 604/162–163, 164.01, 164.08; 600/101, 600/104; 128/830, 831, 840
See application file for complete search history.

(56) References Cited

U.S. PATENT DOCUMENTS

| | | | |
|---|---|---|---|
| 4,027,510 A | 6/1977 | Hiltebrandt | |
| 4,245,623 A | 1/1981 | Erb | |
| 4,790,331 A * | 12/1988 | Okada et al. | 600/585 |
| 4,805,618 A | 2/1989 | Ueda et al. | |
| 4,932,394 A | 6/1990 | Nanaumi | |

(Continued)

FOREIGN PATENT DOCUMENTS

| | | |
|---|---|---|
| EP | 0 891 757 A2 | 1/1999 |
| GB | 2 021 956 A | 12/1979 |

(Continued)

OTHER PUBLICATIONS

PCT Notification of Transmittal of International Search Report and the Written Opinion of the International Searching Authority or the Declaration, PCT/US2012/040003, mailed Jan. 9, 2013, 16 pages.

(Continued)

*Primary Examiner* — Bhisma Mehta
*Assistant Examiner* — Bradley G Thomas, Jr.
(74) *Attorney, Agent, or Firm* — Karen B. King

(57) ABSTRACT

Assemblies and methods of inserting a delivery catheter assembly into a working channel are disclosed. In accordance with some embodiments, a delivery catheter assembly is disclosed in which a tip protector sleeve is locked onto an elongated catheter sheath and slideable over a length of the elongated catheter sheath between a proximal-stop position and a distal-stop position along the elongated catheter sheath.

11 Claims, 18 Drawing Sheets

(56) References Cited

U.S. PATENT DOCUMENTS

| | | | |
|---|---|---|---|
| 5,312,415 A | 5/1994 | Palermo | |
| 5,503,320 A | 4/1996 | Webster et al. | |
| 5,513,628 A | 5/1996 | Coles et al. | |
| 5,741,292 A | 4/1998 | Mendius | |
| 5,741,321 A | 4/1998 | Brennen | |
| 5,743,904 A | 4/1998 | Edwards | |
| 5,749,889 A | 5/1998 | Bacich et al. | |
| 5,935,137 A | 8/1999 | Saadat et al. | |
| 6,053,861 A | 4/2000 | Grossi | |
| 6,162,196 A | 12/2000 | Hart et al. | |
| 6,261,219 B1 | 7/2001 | Meloul et al. | |
| 6,526,979 B1 | 3/2003 | Nikolchev et al. | |
| 6,634,361 B1 | 10/2003 | Nikolchev et al. | |
| 6,705,323 B1 | 3/2004 | Nikolchev et al. | |
| 6,709,667 B1 | 3/2004 | Lowe et al. | |
| 6,726,682 B2 | 4/2004 | Harrington | |
| 6,740,039 B1 | 5/2004 | Rafter et al. | |
| 6,802,825 B2 * | 10/2004 | Ackerman et al. | 604/174 |
| 6,847,336 B1 | 1/2005 | Lemelson et al. | |
| 6,899,105 B2 | 5/2005 | Krueger et al. | |
| 7,025,721 B2 | 4/2006 | Cohen et al. | |
| 7,289,139 B2 | 10/2007 | Amling et al. | |
| 7,338,473 B2 | 3/2008 | Campbell et al. | |
| 7,398,780 B2 | 7/2008 | Callister et al. | |
| 7,736,371 B2 | 6/2010 | Schoepp | |
| 2002/0049423 A1 | 4/2002 | Howell et al. | |
| 2002/0072744 A1 | 6/2002 | Harrington | |
| 2003/0009128 A1 | 1/2003 | Ackerman | |
| 2003/0051735 A1 | 3/2003 | Pavcnik et al. | |
| 2003/0105473 A1 | 6/2003 | Miller | |
| 2003/0158464 A1 | 8/2003 | Bertolero | |
| 2003/0206099 A1 | 11/2003 | Richman | |
| 2004/0010227 A1 * | 1/2004 | Riesenberger et al. | 604/110 |
| 2004/0158127 A1 | 8/2004 | Okada | |
| 2004/0162465 A1 | 8/2004 | Carrillo | |
| 2005/0004512 A1 | 1/2005 | Campbell et al. | |
| 2005/0045184 A1 | 3/2005 | Khera et al. | |
| 2005/0070757 A1 | 3/2005 | Niwa et al. | |
| 2005/0085880 A1 | 4/2005 | Truckai et al. | |
| 2005/0119617 A1 | 6/2005 | Stecker et al. | |
| 2005/0232961 A1 | 10/2005 | Lowe et al. | |
| 2005/0265996 A1 | 12/2005 | Lentz | |
| 2005/0267417 A1 | 12/2005 | Secrest et al. | |
| 2005/0288551 A1 | 12/2005 | Callister et al. | |
| 2006/0116692 A1 | 6/2006 | Ward | |
| 2006/0235433 A1 | 10/2006 | Secrest et al. | |
| 2006/0293560 A1 * | 12/2006 | Nguyen et al. | 600/104 |
| 2007/0088247 A1 | 4/2007 | Bliweis et al. | |
| 2007/0213590 A1 | 9/2007 | Squicciarini | |
| 2008/0041394 A1 * | 2/2008 | Swann et al. | 128/831 |
| 2008/0154256 A1 | 6/2008 | Payne et al. | |
| 2010/0063360 A1 | 3/2010 | Harrington et al. | |
| 2011/0094519 A1 | 4/2011 | Gopal | |

FOREIGN PATENT DOCUMENTS

| | | |
|---|---|---|
| GB | 2 156 224 A | 10/1985 |
| WO | WO 99/15116 | 4/1999 |

OTHER PUBLICATIONS

PCT Notification Concerning Transmittal of International Preliminary Report on Patentability (Chapter 1 of the Patent Cooperative Treaty) PCT/US2012/040013, mail date Dec. 12, 2013, total 8 pages.

PCT Notification Concerning Transmittal of International Preliminary Report on Patentability (Chapter 1 of the Patent Cooperative Treaty) PCT/US2012/040003, mail date Dec. 12, 2013, total 10 pages.

PCT Invitation to Pay Additional Fees, PCT/US2006/012952, date mailed Feb. 2, 2007, total 8 pages.

PCT Notification of Transmittal of International Search Report and the Written Opinion of the International Searching Authority or the Declaration, PCT/US2006/012952, mail date Apr. 27, 2007, total 18 pages.

PCT Notification Concerning Transmittal of International Preliminary Report on Patentability (Chapter 1 of the Patent Cooperative Treaty), and the PCT Written Opinion of the International Searching Authority PCT/US2006/012952, mail date Jan. 10, 2008, total 12 pages.

Conceptus, Inc., "U.S. Physician Training Manual", Essure—Permanent Birth Control, retrieved from the Internet at: http://www.essuremd.com/portals/essuremd/PDFs/PST/CC1687__Essure__Training__Manual.pdf, CC-1687, 70 pages, (Jan. 7, 2008).

Conceptus, Inc., "ESS305 Purple Handle", Essure—Permanent Birth Control, retrieved from the Internet at: http://www.essuremd.com/portals/essuremd/PDFs/TopDownloads/L3002%2009__09__09%20smaller.pdf, L3002, 7 pages, (Oct. 21, 2010).

PCT Notification of Transmittal of International Search Report and the Written Opinion of the International Searching Authority or the Declaration, PCT/US2012/040013, mailed Sep. 5, 2012, 18 pages.

PCT Invitation to Pay Additional Fees, PCT/US2012/040003, mailed Sep. 10, 2012, 4 pages.

Bayer Essure Inc. Office Action for U.S. Appl. No. 13/323,741 mailed Jun. 27, 2014.

Bayer Essure Inc. Office Action for U.S. Appl. No. 13/323,741 mailed Dec. 19, 2013.

* cited by examiner

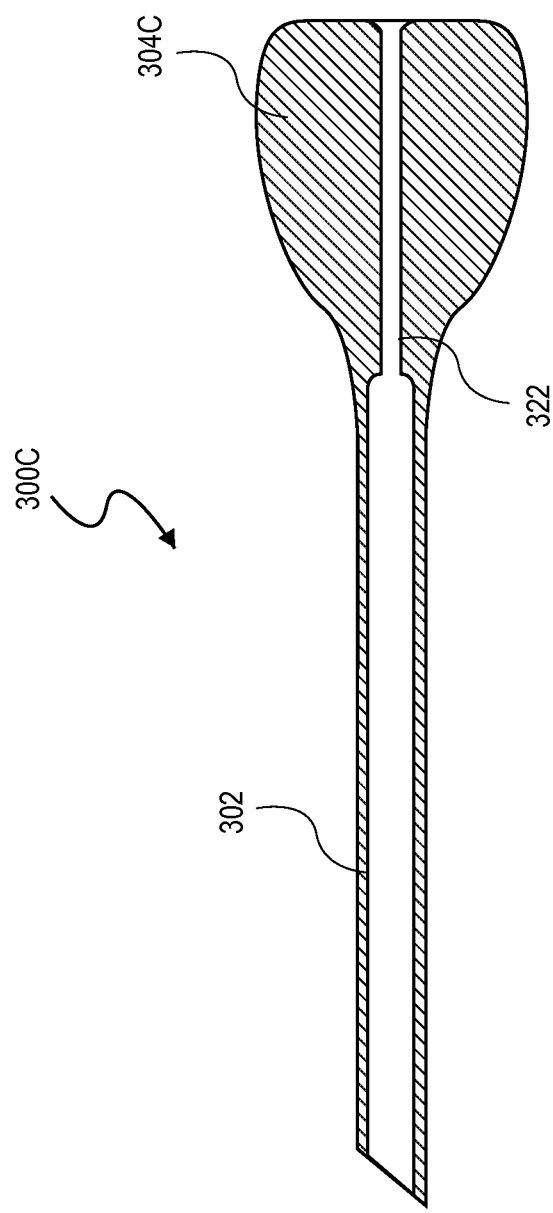

TIP PROTECTOR SLEEVE

BACKGROUND

Embodiments of the present invention relate to the field of minimally invasive surgical medical devices and medical procedures. More specifically, embodiments of the present invention relate to devices and methods used for transcervical gynecological procedures.

Female contraception and sterilization may be affected by transervically introducing an object into a fallopian tube to inhibit conception. Devices, systems and methods for such a contraceptive approach have been described in various patents and patent applications assigned to the present assignee. For example, U.S. Pat. Nos. 6,526,979, 6,634,361, U.S. patent application Ser. No. 11/165,733 published as U.S. Publication No. 2006/0293560 and U.S. patent application Ser. No. 12/605,304 describe transcervically inserting an insert (also referred to as implant and device) into an ostium of a fallopian tube and mechanically anchoring the insert within the fallopian tube. One example of such an assembly is known as "Essure"® from Conceptus, Inc. of Mountain View, Calif. Tissue in-growth into the "Essure"® insert provides long-term contraception and/or permanent sterilization without the need for surgical procedures.

The insert may be delivered to the fallopian tube with a delivery catheter assembly such as the one illustrated in FIG. 1. The delivery catheter assembly 100 is formed of a control device 102 such as a handle, an elongated sheath 104, and an insert 106. The delivery catheter assembly 100 may be transcervically positioned into the uterus and the fallopian tubes via a hysteroscope system.

Referring to FIG. 2 the hysteroscope system 200 may include a working channel 202 into which the delivery catheter assembly is inserted. Advancement of the delivery catheter system within the uterus and the fallopian tubes is usually facilitated by distending the uterus with a distention fluid, such as saline, and viewing the placement with the hysteroscope system. A valve clamp 208, such as a ball valve clamp, and an access port 206 are positioned at the tip of the working channel 202. Closing the valve clamp 208 may seal the entrance of the working channel 202 to prevent a distention fluid from leaking out of the access port 206. A sealing cap 230 including a pierceable end 232 can be placed over the access port 206 to prevent distention fluid from leaking out of the hysteroscope system when a delivery catheter assembly occupies the working channel of the hysteroscope system.

An introducer 220 may be used in order to prevent damaging the tip the elongated sheath 104 or insert 106 of the delivery catheter assembly 100 during insertion through the pierceable end 232 of the sealing cap 230 and access port 206, and into the working channel 202 of the hysteroscope system 200. Introducer 220 includes a sheath portion 222 and slit opening 224 to aid in grasping and in the removal of the introducer 220. The introducer 220 is inserted through the pierceable end 232 of the sealing cap 230 and into the working channel 202 prior to inserting the delivery catheter assembly 100. When the introducer 220 is inserted through the sealing cap 230, fluid can spray out of the introducer 220 and onto the physician or physician's assistant. The amount of fluid spray-back can be significant depending on the distention fluid pressure during the procedure.

Referring to FIG. 3, after placing the introducer 220 into the working channel 202, the tip of delivery catheter assembly 100 is inserted into the slit opening 224 and through the sheath 222 of the introducer 220 in order to advance the delivery catheter assembly 100 into the working channel 202 of the hysteroscope system. This is typically performed as soon as possible after placement of the introducer 220 into the working channel 202 in order to minimize the amount of fluid spray-back from the introducer. The introducer 220 may then be removed or may be kept in place throughout the procedure. After insertion of the delivery catheter assembly 100 into the introducer 200, an amount of distention fluid may still leak from between the introducer and elongated sheath 104 of the delivery catheter assembly 100.

SUMMARY

Embodiments of the present invention generally provide assemblies and methods of inserting a delivery catheter into a working channel of an endoscope, such as a hysteroscope system for accessing a female reproductive system. While embodiments of the invention are described with reference to a hysteroscope system, it is understood that the embodiments are not limited to such and may also be compatible with other optical surgical devices. In one aspect, embodiments of the invention describe a tip protector sleeve which functions as an introducer and protects the tip of a delivery catheter assembly when piercing a sealing cap, as well as during insertion through an access port, into the working channel and past a valve clamp of a hysteroscope system. In another aspect, embodiments of the invention describe a method and system which may reduce the amount of fluid spray-back and leakage associated with inserting a delivery catheter assembly into the working channel of a hysteroscope system.

One embodiment of the present invention relates to a delivery catheter assembly which may be used to deliver an insert to an ovarian pathway (e.g. a fallopian tube) of a female body. The delivery catheter assembly may include a control device, an elongated catheter sheath having a distal end and a proximal end connected to the control device, and a tip protector sleeve. The tip protector sleeve may be locked onto the elongated catheter sheath and slideable over a length of the elongated catheter sheath between a proximal-stop position and a distal-stop position along the elongated catheter sheath. The delivery catheter assembly may further include an interference stop which determines the distal-stop position and prevents the tip protector sleeve from sliding off of the distal end of the elongated catheter sheath. For example, the interference stop may include a male interference part which interferes with sliding of a female interference part over the elongated catheter sheath. The male interference part may be fixed to the elongated catheter sheath, and the tip protector sleeve may comprise the female interference part. The tip protector sleeve may additionally incorporate a sealing valve to reduce the amount of fluid spray-back and leakage associated with inserting the delivery catheter assembly into the working channel of a hysteroscope system Another embodiment of the present invention relates to a method of forming a delivery catheter assembly which includes sliding a tip protector sleeve over a distal end of an elongated catheter sheath and toward a control device, and then fixing a bump onto a distal region of the elongated catheter sheath. Alternatively, the bump may be fixed onto the distal region of the elongated catheter sheath, and then the tip protector sleeve is slid over a proximal end of the elongated catheter sheath toward the bump prior to attaching the control device to the elongated catheter sheath. The control device may prevent the tip protector sleeve from sliding off a proximal end of the elongated sheath and define, in part, a proximal-stop position. The bump may prevent the tip protector sleeve from sliding off of a distal end of the elongated catheter sheath and define, in part, a distal-stop position. In an embodiment, the bump may be fixed onto a distal region of the elongated catheter sheath by crimping a band onto the elongated catheter sheath. It is not necessary to crimp the entire length of the band, and only a proximal end of the band is crimped onto the elongated catheter shaft in an embodiment.

Another embodiment of the present invention relates to a method of delivering an insert into a body lumen such as an ovarian pathway (e.g. a fallopian tube) of a female body. Utilizing a delivery catheter assembly in accordance with embodiments of the invention the tip protector sleeve is positioned at the distal-stop position, and the tip protector sleeve is inserted through a pierceable end of a sealing cap, through an access port of a hysteroscope system and into a working channel of the hysteroscope system. In accordance with embodiments of the invention, the distal end of the elongated catheter sheath and insert are inserted through the pierceable end of the sealing cap, through the access port and into the working channel of the hysteroscope system simultaneously with the tip protector sleeve in the distal-stop position. The distal end of the elongated catheter sheath and insert may then be advanced through the tip protector sleeve and beyond the hysteroscope system to a target location within the body lumen where the insert is deployed within the body lumen. In an embodiment, the tip protector sleeve is advanced through the sealing cap into the working channel until a flanged mechanical stop, such as a bead or flared portion, abuts the sealing cap (or access port if a sealing cap is not utilized) prior to advancing the elongated sheath and insert to the target location.

BRIEF DESCRIPTION OF THE DRAWINGS

FIG. 10 is a cross-sectional side view illustration of a tip protector sleeve in accordance with an embodiment of the invention.

DETAILED DESCRIPTION

Embodiments of the present invention generally provide assemblies and methods of inserting a delivery catheter into a working channel of an endoscope, such as a hysteroscope system or other optical surgical device for accessing a female reproductive system. Various embodiments and aspects will be described with reference to details discussed below and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

Figure 1:
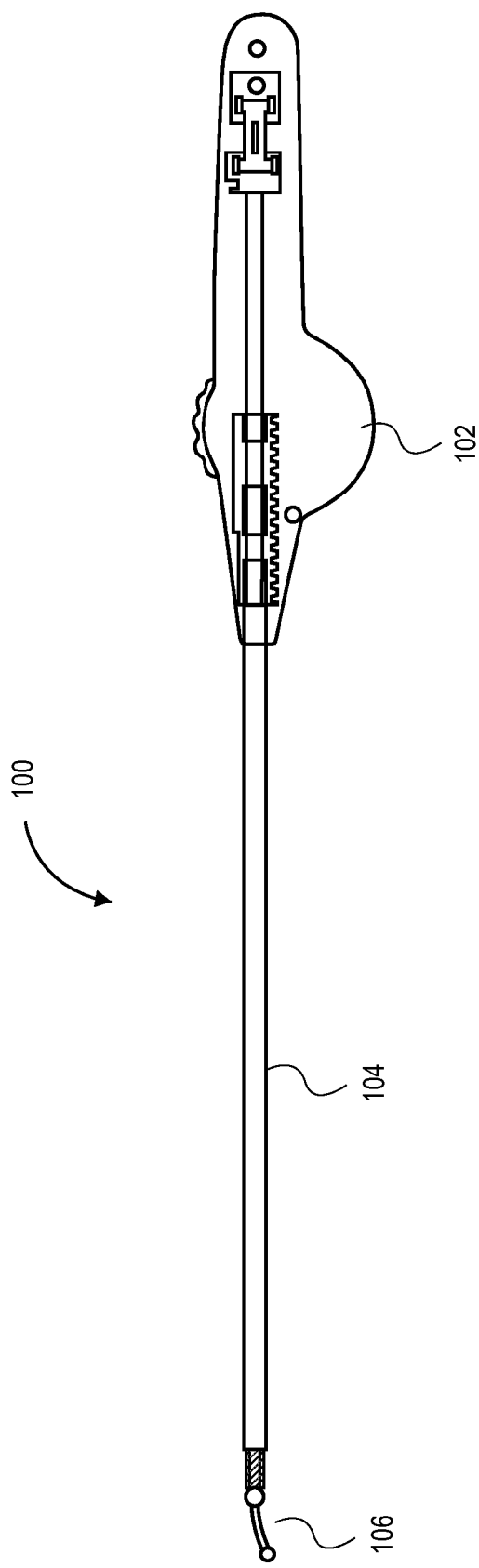
FIG. 1 is a cross-sectional side view illustration of a delivery catheter assembly.
Figure 2:
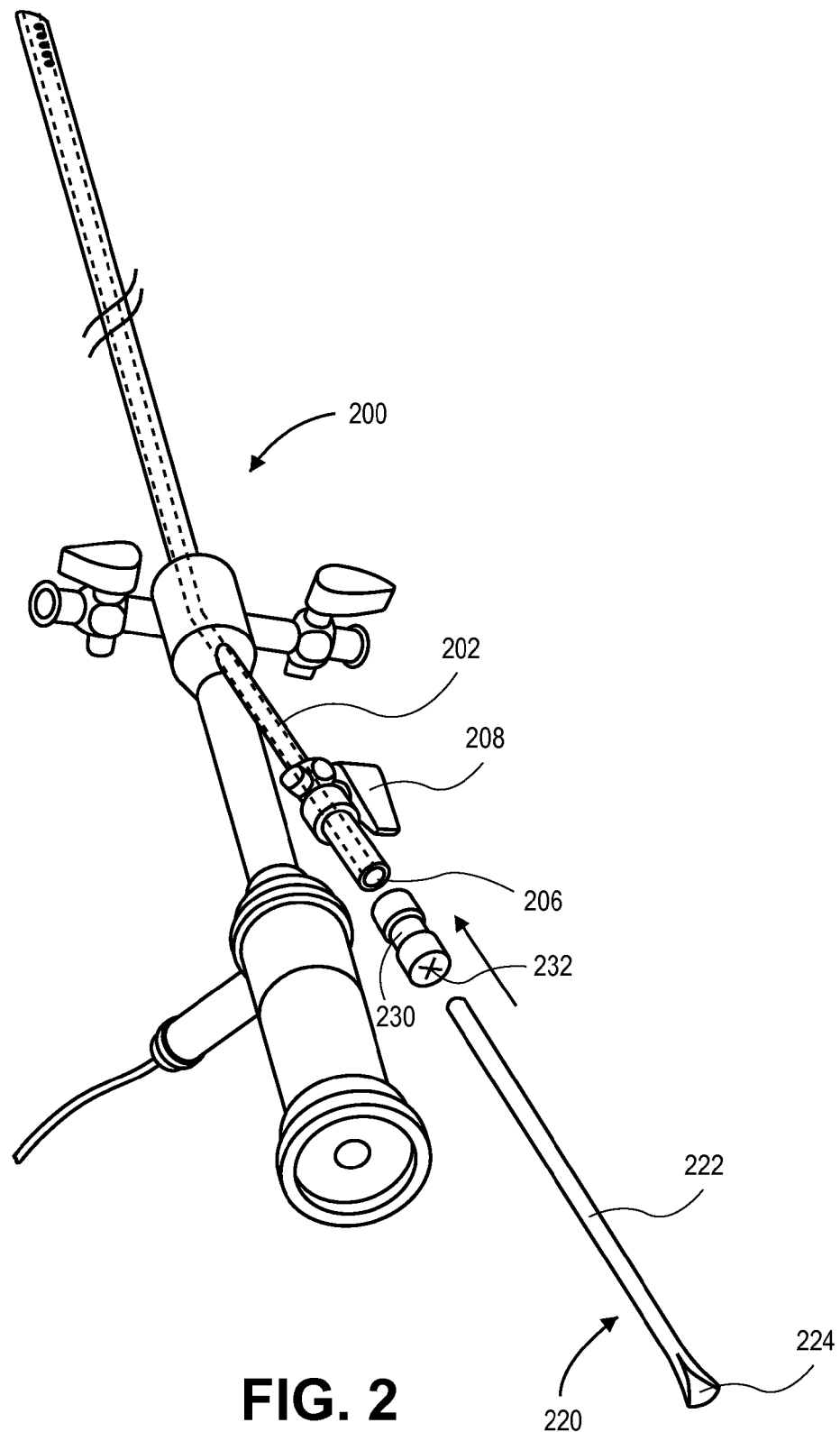
FIG. 2 is an isometric view illustration of a hysteroscope system and an introducer.
Figure 3:
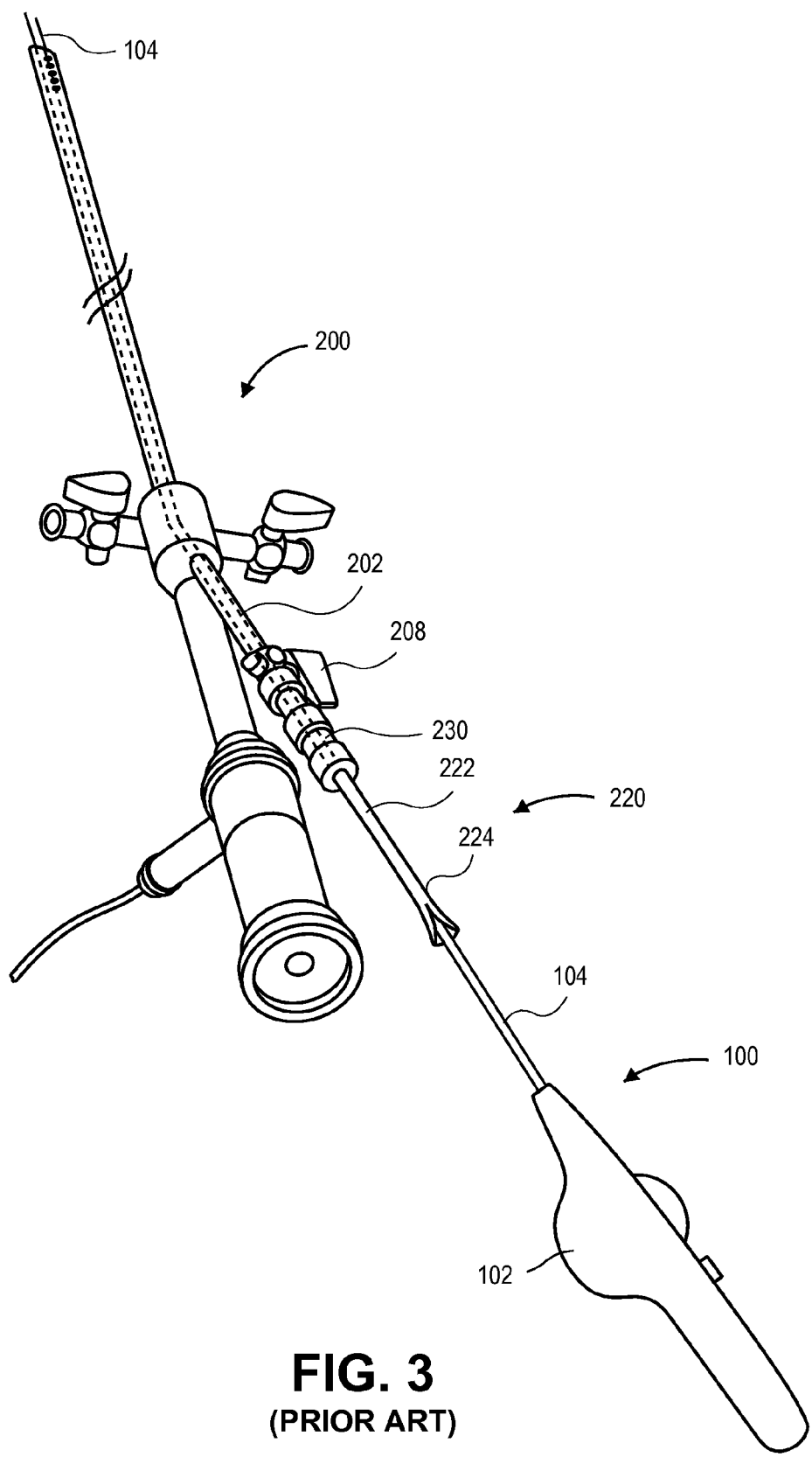
FIG. 3 is an isometric view illustration of a delivery catheter assembly inserted into an introducer and working channel of a hysteroscope system.
Figure 4:
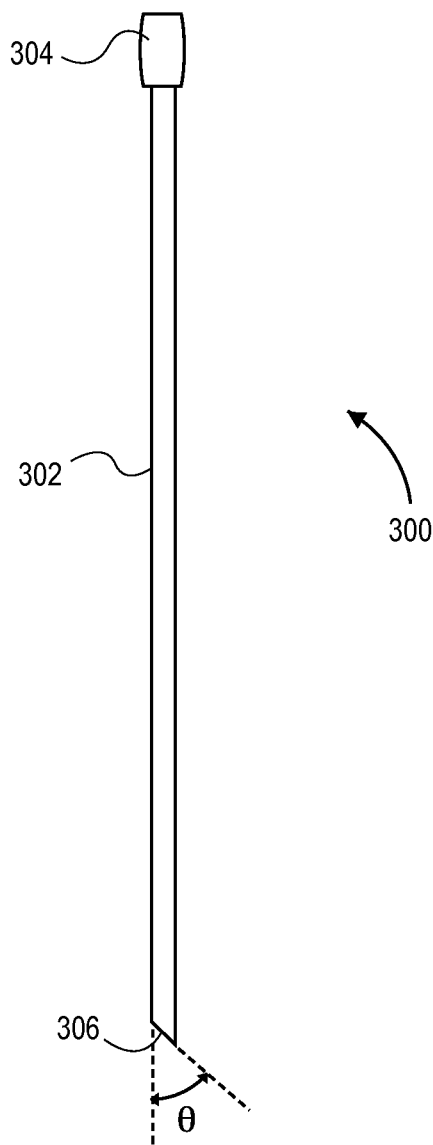
FIG. 4 is a side view illustration of a tip protector sleeve in accordance with an embodiment of the invention.

In an embodiment, a delivery catheter assembly includes a control device, an elongated catheter sheath having a distal end and a proximal end connected to the control device, and a tip protector sleeve. Referring to the FIG. 4 the tip protector sleeve 300 may include an elongated shaft 302, a flanged mechanical stop 304 at a proximal end, and a distal end 306. The distal end 306 can be flat or angled to assist with piercing of a sealing cap. In an embodiment, the distal end 306 has an approximately 45 degree angled tip. Elongated shaft 302 may be formed of a material and to a thickness which can be molded and does not buckle when piercing a sealing cap. For example, elongated shaft 302 may be formed of a material such as polyether ether ketone (PEEK).

Flanged mechanical stop 304 may provide variety of functions, be formed of a variety of materials and have a variety of shapes and sizes as will be explained in further detail with regard to FIGS. 5A-12C. For example, flanged mechanical stop 304 may be formed of a moldable material such as polycarbonate, or from the same material as the elongated shaft 302. Flanged mechanical stop 304 may be sized and shaped larger than the inside diameter (ID) of a corresponding access port opening to a working channel or pierceable end of a sealing cap if present in order to act as a stop mechanism that controls the insertion depth of the tip protector sleeve 300 into the working channel. Flanged mechanical stop 304 may also be sized and shaped to be gripped by an operator's hand to assist with sliding of the tip protector sleeve 300 over a length of the elongated catheter sheath 404 of a catheter assembly. In this respect, one function may be as a handle at the proximal end of the tip protector sleeve 300. Flanged mechanical stop 304 may also incorporate a sealing valve to reduce the amount of fluid spray-back and leakage associated with inserting the delivery catheter assembly into a working channel.

Figure 5A:
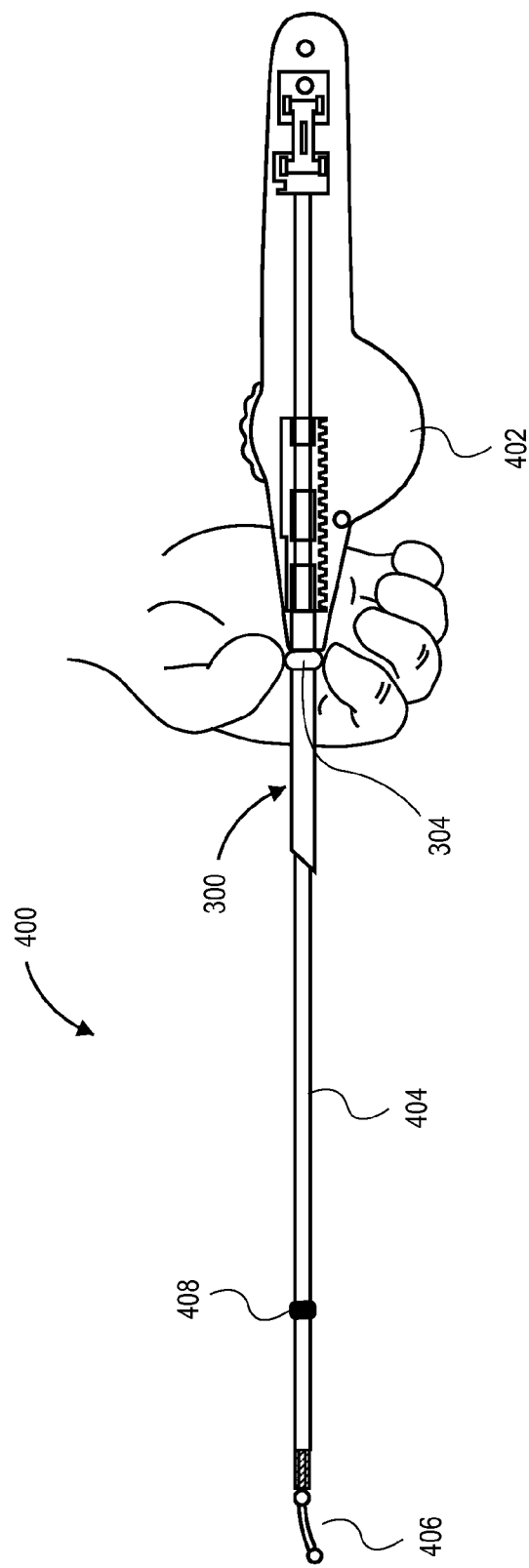
FIG. 5A is a side view illustration of a delivery catheter assembly with a tip protector sleeve at a proximal-stop position in accordance with an embodiment of the invention.
Figure 5B:
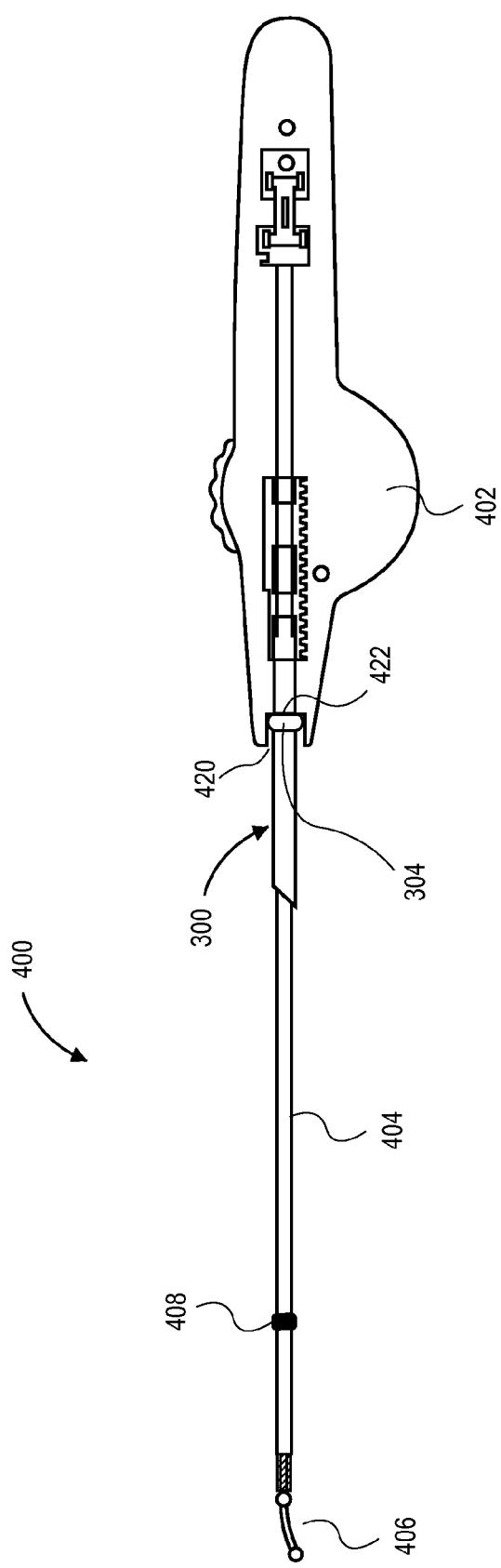
FIG. 5B is a side view illustration of a delivery catheter assembly with a flanged mechanical stop of a tip protector sleeve in a cavity of a control device in accordance with an embodiment of the invention.
Figure 5C:
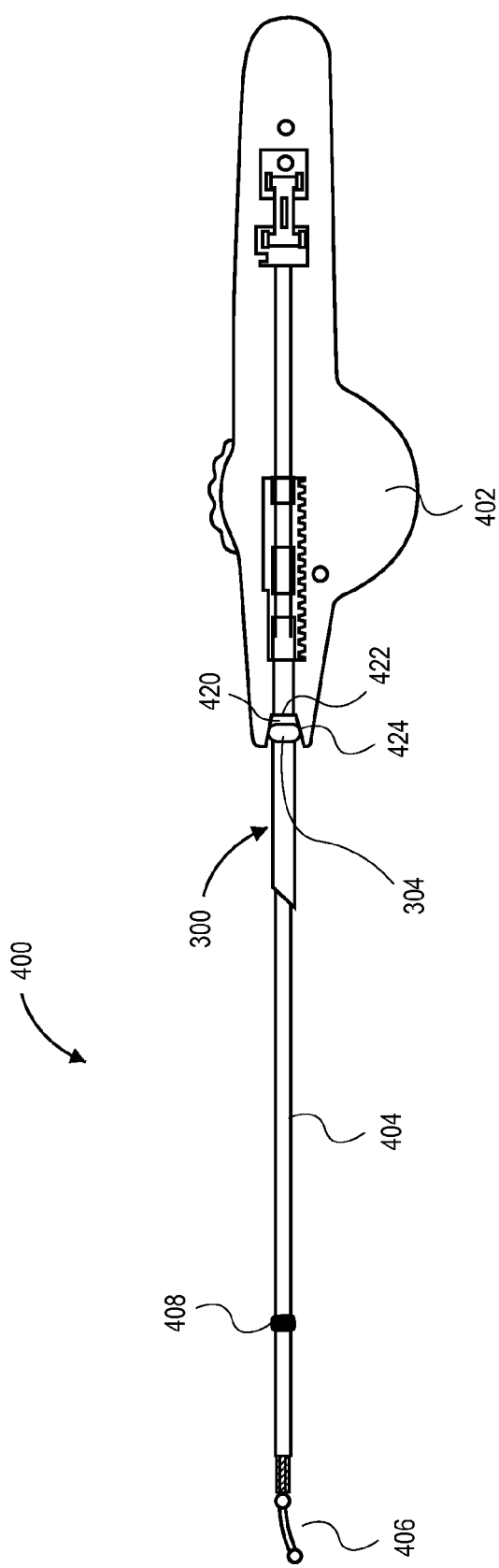
FIG. 5C is a side view illustration of a delivery catheter assembly with a tip protector sleeve fastened into the proximal-stop position by a friction fitting in accordance with an embodiment of the invention.
Figure 5D:
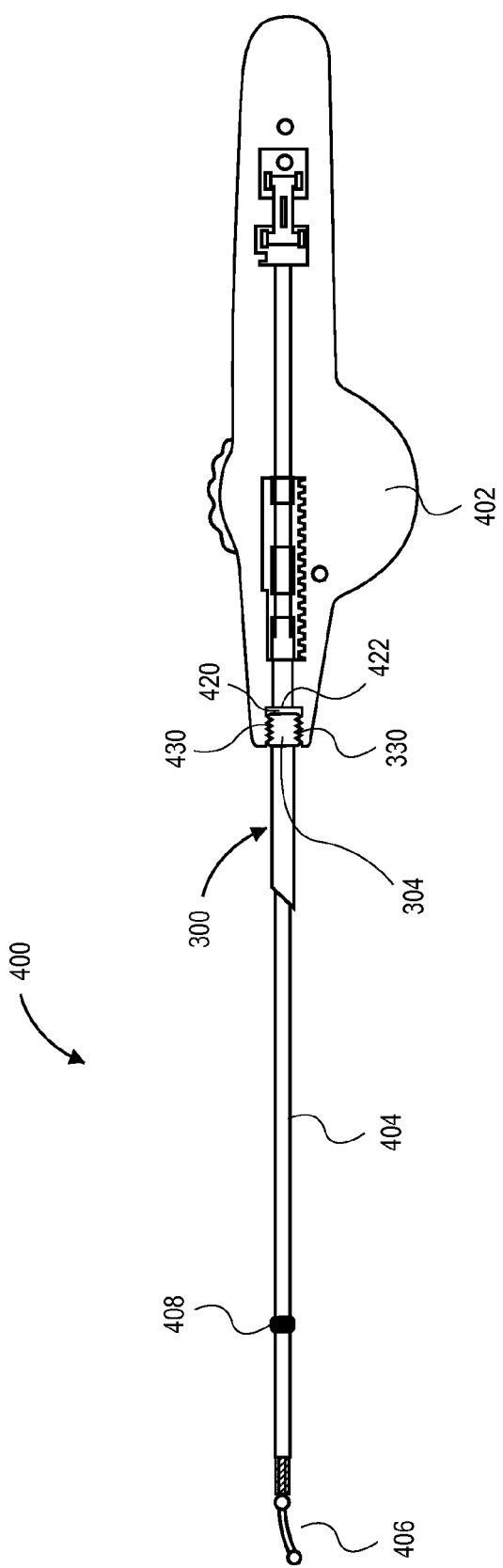
FIG. 5D is a side view illustration of a delivery catheter assembly with a tip protector sleeve screwed into the proximal-stop position in accordance with an embodiment of the invention.
Figure 6:
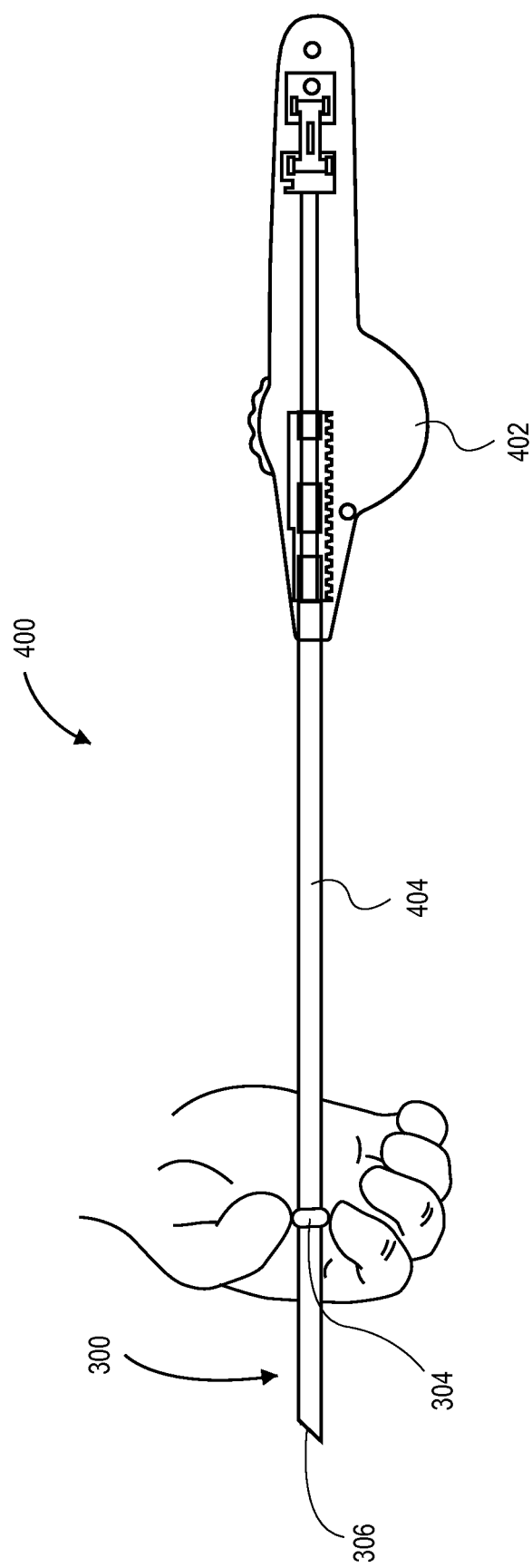
FIG. 6 is a side view illustration of a delivery catheter assembly with a tip protector sleeve at a distal-stop position in accordance with an embodiment of the invention.

Referring to FIGS. 5A-6, a delivery catheter assembly 400 in accordance with embodiments of the invention is illustrated in which the tip protector sleeve 300 is locked onto and slideable over a length of the elongated catheter sheath 404.

The delivery catheter assembly 400 may be formed by sliding a tip protector sleeve 300 over a distal end of an elongated catheter sheath 404 and toward a control device 402, and then fixing a bump 408AC onto a distal region of the elongated catheter sheath 404. Alternatively, the bump 408 may be fixed onto the distal region of the elongated catheter sheath 404, and then the tip protector sleeve 300 is slid over a proximal end of the elongated catheter sheath 404 toward the bump 408 prior to attaching the control device 402 to the elongated catheter sheath 404. The control device 402 may prevent the tip protector sleeve 300 from sliding off a proximal end of the elongated sheath 404 and define, in part, a proximal-stop position. The bump 408 may prevent the tip protector sleeve 300 from sliding off of a distal end of the elongated catheter sheath 404 and define, in part, a distal-stop position. An operator may grip the flanged mechanical stop 304 by hand, for example between a thumb and index finger, and slide the tip protector sleeve over the elongated catheter sheath 404 between the proximal-stop and distal-stop positions.

FIG. 5A is an illustration of the tip protector sleeve 300 positioned at a proximal-stop position. In the embodiment illustrated in FIG. 5A, the flanged mechanical stop 304 abuts a distal end of the control device 402, though other proximal-stop positions along the elongated catheter sheath 404 are contemplated in accordance with embodiments of the invention. For example, FIGS. 5B-5D are illustrations of embodiments in which the control device 402 is configured to allow flanged mechanical stop 304 to slide within a cavity 420 located at a distal portion of the control device 402. Such embodiments may be useful during operation in order to utilize the full working length of the elongated catheter sheath 404. In this manner, the distal end of the control device 402 can be advanced to abut the access port 206 of the hysteroscope system or the pierceable end 232 of a sealing cap 230 if desired during operation. Alternatively, the distal end of the control device 402 can be advanced over the access port 206 of the hysteroscope system or over sealing cap 230 and the flanged mechanical stop 304 is allowed to abut the access port 206 or the pierceable end 232 of the sealing cap 230. As illustrated in FIG. 5B, flanged mechanical stop 304 may be slid into cavity 420 to abut a back wall 422 of the cavity at the proximal-stop position. Flanged mechanical stop 304 may be also configured to fasten onto the handle 402 at the proximal-stop position. For example, FIG. 5C is an illustration of an embodiment in which flanged mechanical stop 304 may be slid into cavity 420 and fastened into the proximal-stop position by a friction fitting with sloped walls 424 of the cavity. FIG. 5D is an illustration of an embodiment in which flanged mechanical stop 304 may be screwed into cavity 420 in which threads 330 on flanged mechanical stop 304 mate with threads 430 inside cavity 420 to fasten tip protection sleeve 300 in the proximal-stop position. In an embodiment, a suitable fastening mechanism for fastening tip protector sleeve 300 onto control device 402 is able to hold the tip protector sleeve 300 in the proximal-stop position during withdrawal of the delivery catheter assembly 400 from the working channel of the hysteroscope system.

Referring now to FIG. 6 an operator may slide the tip protector sleeve over the elongated catheter sheath 404 between the proximal-stop position and the distal-stop position illustrated in FIG. 6. As illustrated, the distal end 306 of tip protector sleeve 300 may extend distally beyond a distal end of the elongated catheter sheath 404 and insert 406 when at the distal-stop position. In this manner, the tip protector sleeve 300 may protect the distal ends of the elongated catheter sheath 404 and insert 406 during piercing of a sealing cap and during insertion into the working channel and past a valve clamp of the hysteroscope system.

An interference stop may determine the distal-stop position and prevent the tip protector sleeve 300 from sliding off of the distal end of the elongated catheter sheath 404. In an embodiment, the interference stop includes a male interference part which interferes with sliding of a female interference part over the elongated catheter sheath. Referring again to FIG. 5A, the male interference part may comprise a bump 408 fixed to the elongated catheter sheath 404. Bump 408 may be formed along only a portion of the circumference of the elongated sheath, or may encircle the circumference of the elongated sheath. In an embodiment, bump 408 is a band fixed to and encircling the circumference of the elongated catheter sheath. In an embodiment, bump 408 is fixed to the elongated catheter sheath 404 with a sufficient shear strength to ensure that the tip protector sleeve may be removed from a working channel of a hysteroscope system along with removal of the elongated catheter sheath 404.

Figure 7:
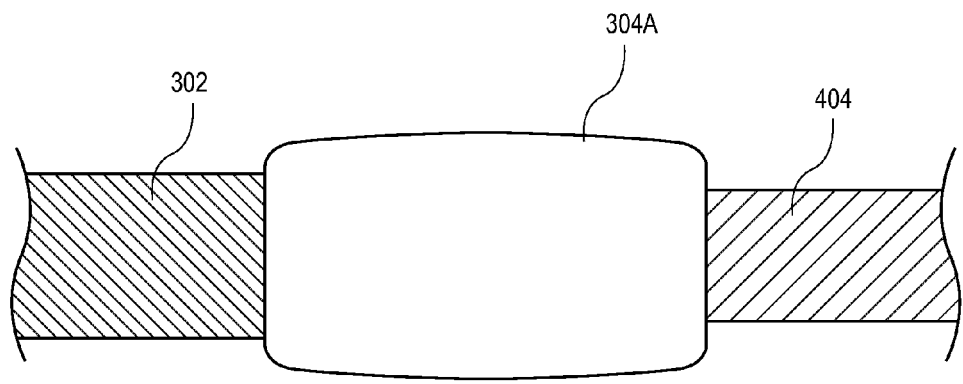
FIG. 7 is a close-up side view illustration of the proximal end of a tip protector sleeve over an elongated catheter sheath in accordance with an embodiment of the invention.
Figure 8:
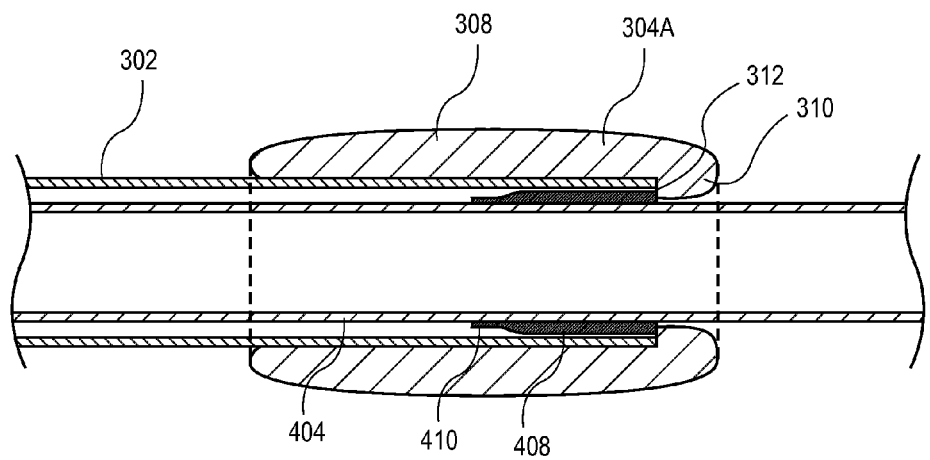
FIG. 8 is a close-up cross-sectional side view illustration of the proximal end of a tip protector sleeve over an elongated catheter sheath in accordance with an embodiment of the invention

FIG. 7 is a close-up side view illustration of the proximal end of a tip protector sleeve over an elongated catheter sheath in accordance with an embodiment of the invention. FIG. 8 is a close-up cross-sectional side view illustration of the proximal end of a tip protector sleeve over an elongated catheter sheath in accordance with an embodiment of the invention. As illustrated in FIGS. 7-8, flanged mechanical stop may be a bead 304A having a barrel-like shape, though embodiments of the invention are not limited to such a shape. In an embodiment, bead 304A is fixed to shaft 302 with an adhesive.

Referring to FIG. 8, in an embodiment bead 304A may be fixed to a proximal end of the elongated shaft 302. Bead 304A may include a distal portion 308 surrounding the proximal end of the elongated shaft 302, a shoulder portion 310 extending proximally of the elongated shaft 302, and a backstop 312. The distal portion 308 may be fixed to the elongated shaft 302 with an adhesive. In an embodiment, the backstop 312 abuts the proximal end of the elongated shaft 302. Backstop 312 may also have a height which is greater than a thickness of the elongated shaft 302. For example, the height may be defined as the distance between and inside diameter (ID) of the backstop and an ID of the distal portion 308 of the bead 304A. In accordance with various embodiments of the invention, the dimensions and location of the backstop 312 as they relate to the dimensions and location of bump 410 create an interference stop which determines the distal-stop position and prevents the tip protector sleeve from sliding off of the distal end of the elongated catheter sheath 404.

In an embodiment, the tip protector sleeve 300 is locked onto an "Essure"® delivery catheter assembly. In such an embodiment, the ID of elongated catheter sheath 404 may be between 0.0405 and 0.0420 inches and the outside diameter (OD) of elongated catheter sheath 404 may be between 0.0538 and 0.0560 inches. Elongated catheter sheath 404 may be formed of a polyether block amide also known under the trade name PEBAX. The OD of elongated catheter sheath 404 may be used to determine the ID of bump 408. In an embodiment, bump 408 may have an ID between 0.0545 and 0.0555 inches and an OD between 0.0575 and 0.0580 inches. In one embodiment, the ID of bump 408 may be smaller than the OD of the elongated catheter sheath 404. In another embodiment, the OD of the elongated catheter sheath 404 is smaller than the ID of bump 408. For example, the OD of the elongated catheter sheath 404 may be between 0.0538 and 0.0542 inches.

Bump 408 may be a band that is fixed to and encircles the elongated catheter sheath. Bump may be fixed to the elongated catheter sheath 404 by a variety of mechanisms including adhesive and crimping. In an embodiment, bump 408 is formed of a material which is strong enough to resist deformation during operation of the delivery catheter assembly, yet malleable enough to be suitable for crimping. For example, stainless steel possesses suitable strength and malleability. In an embodiment, only a distal end 410 of the band is crimped onto the elongated catheter sheath, as illustrated in FIG. 8. This leaves the proximal end, with the original OD between 0.0575 and 0.0580 inches to act as the male interference part which interferes with the ID of backstop 312 functioning as a part of the female interference part. While an embodiment of bump 408 is described in detail in FIG. 8 in operable relationship with bead 304A, it is understood that bump 408 can be in operable relationship with other flanged mechanical stops, such as those illustrated in FIGS. 9-11C.

Still referring to FIG. 8, bead 304A may be formed of a variety of materials and have a variety of shapes and sizes to perform a variety of functions. In one aspect, bead 304A may be sized and shaped larger than the inside diameter (ID) of a corresponding access port opening to a working channel or pierceable end of a sealing cap if present in order to act as a stop mechanism that controls the insertion depth of the tip protector sleeve 300 into the working channel. In one aspect, bead 304A may perform the function as a handle for gripping by the operator. In another aspect, bead 304A may include a backstop 312 which functions as part of the female interference part. In an embodiment, bead 304A has an OD of approximately 0.112 inches. The distal portion 308 of bead 304A may have an ID of approximately 0.070 and may be bonded to the OD of elongated shaft 302. Backstop 312 may have an ID which is smaller than an OD of the proximal end of bump 408. For example, backstop 312 may have an ID between 0.0565 and 0.0575 inches. In such an embodiment, backstop 312 has a height that extends from the ID of back stop 312 to the ID of the distal portion 308 of the bead 304, or approximately 0.013 inches.

Figure 12A:
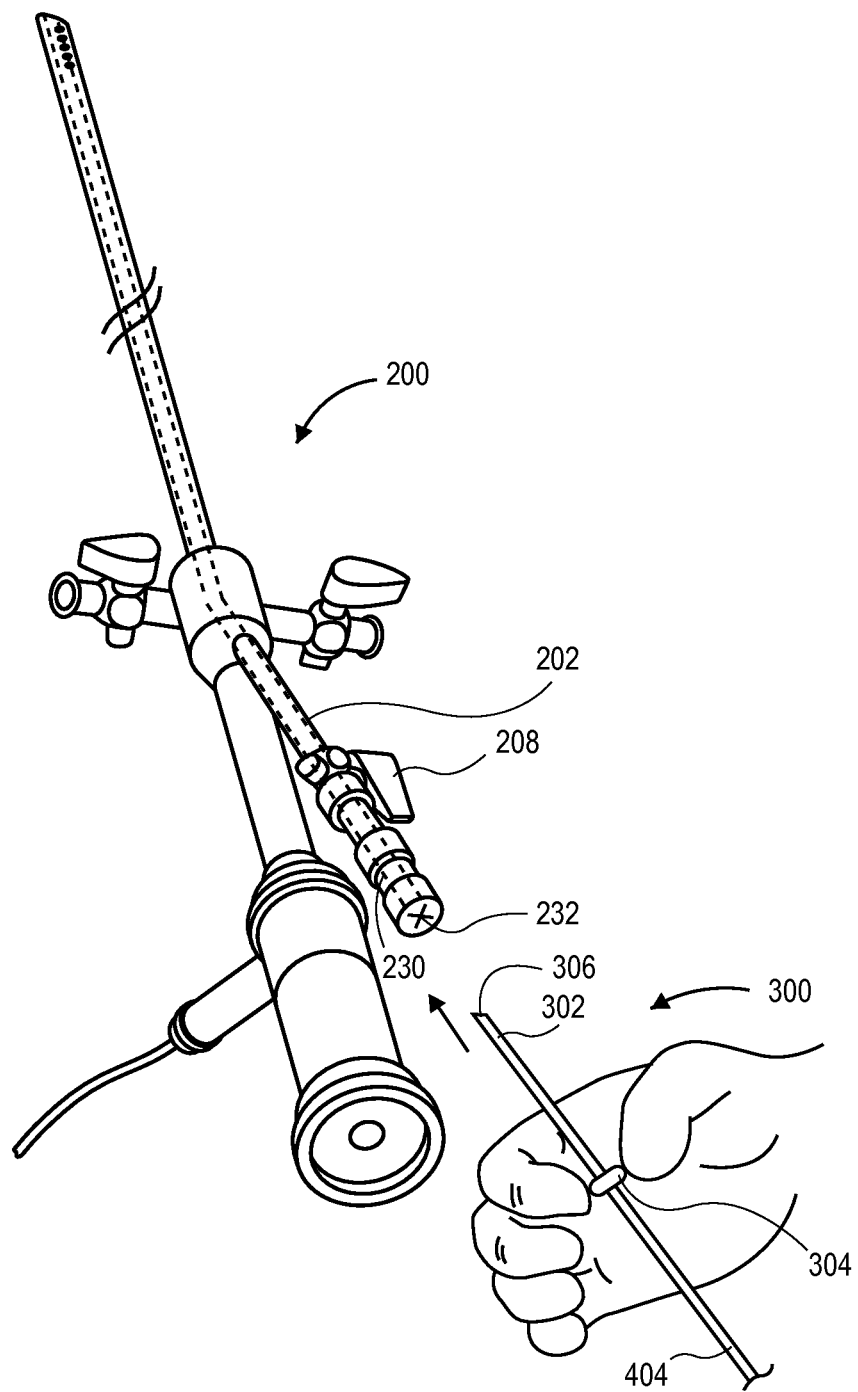
FIGS. 12A-12C are isometric view illustrations of inserting a delivery catheter assembly into a working channel of a hysteroscope system in accordance with an embodiment of the invention.

In accordance with embodiments of the invention tip protector sleeve 300 may be locked onto the delivery catheter assembly 400. Shaft 302 may be used to pierce a sealing cap and protect the tip of the insert 406, elongated catheter sheath 404 or guidewire during insertion into the working channel and past a valve clamp of a hysteroscope system. In an embodiment, the shaft 302 and elongated catheter sheath 404 may be advanced into a working channel of a hysteroscope system without allowing a significant amount of fluid (e.g. saline) spray-back or leakage from the delivery catheter assembly. The elongated catheter sheath 404 may additionally be slid through the shaft 302 to deliver the insert 406 to a body lumen, while the delivery catheter assembly 400 does not allow a significant amount of fluid leakage. Referring now to FIG. 12A, the shaft 302 may pierce the pierceable end 232 of a sealing cap 230 with the tip of the shaft 306. The outside diameter of the shaft 302 may fit tightly in the pierceable end 232 effectively creating a water tight seal between the sealing cap 230 and tip protector sleeve 300.

The reduction of fluid spray-back and leakage may also be achieved by controlling the shape and dimensions of the tip protector sleeve 300 as it interacts with the elongated catheter sheath 404 and bump 408. In an embodiment, shaft 302 may be approximately 2.82 inches long from the proximal end to the distal end of the tip 306, which may be angled. Shaft 302 may have an ID between 0.0585 and 0.0605 inches and an OD between 0.0690 and 0.0710 inches. The shaft 302 ID may be selected to not allow for fluid to flow proximally between the shaft 302 and elongated catheter sheath 404 (and bump 408), while still allowing for the elongated catheter sheath 404 to slide and be advanced through the shaft 302. In such and embodiment, a minimum clearance between the ID of the elongated shaft 302 (e.g. 0.059 inches) and the OD of the elongated catheter sheath 404 (e.g. 0.055 inches) provides sufficient resistance to spray-back and leakage. Such a minimum clearance may be effective for overlapping constant diameters of the elongated shaft 302 and elongated catheter sheath 404.

Figure 9:
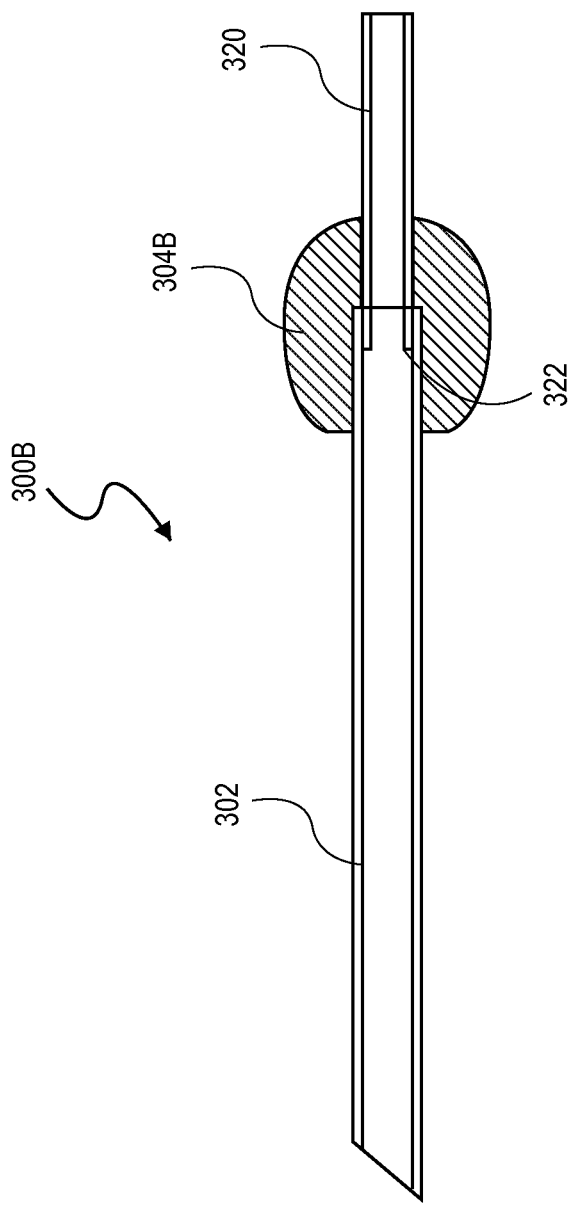
FIG. 9 is a cross-sectional side view illustration of a tip protector sleeve in accordance with an embodiment of the invention.

Referring now to FIG. 9, an embodiment for tip protector sleeve 300B is illustrated. As illustrated in FIG. 9, tip protector sleeve 300B includes an elongated shaft 302, a bead 304B and inner shaft 320. Tip protector sleeve 300B operates similarly as tip protector sleeve 300 with one difference being that backstop 322 is the distal end of inner shaft 320. In such an embodiment, the shape and dimensions of tip protector sleeve 300B are controlled so that bump 408 interferes with movement of the distal end, backstop 322 of inner shaft 320. In such an embodiment, bead 304B may be sized and shaped to act as a stop mechanism that controls the insertion depth of the tip protector sleeve 300B into the working channel and may perform the function as a handle for gripping by the operator Referring now to FIG. 10, another embodiment for tip protector sleeve 300C is illustrated. As illustrated in FIG. 10, tip protector sleeve 300C includes an elongated shaft 302, a neck portion 332, and a flared portion 304C. Tip protector sleeve 300C operates similarly as tip protector sleeves 300 and 300B. One difference is that the neck portion 332 operates as the backstop for bump 408. The neck portion 332 may be integrally formed with the elongated shaft 302 or be a separate member bonded to the inside diameter of elongated shaft 302 Likewise flared portion 304C may be integrally formed with the elongated shaft 302 or be a separate member bonded to the outside diameter of elongated shaft 302. In such an embodiment, flared portion 304C may be sized and shaped to act as a flanged mechanical stop that controls the insertion depth of the tip protector sleeve 300C into the working channel and may perform the function as a handle for gripping by the operator.

Embodiments of the invention are also envisioned in which the elongated catheter sheath 404 does not have a constant OD along its length. In accordance with some embodiments, the tip protector sleeve 300 may include a change in ID or a valve to accommodate variations in the OD of the elongated catheter sheath 404, or to more effectively seal an elongated catheter sheath 404 with a constant OD. Referring again to FIG. 9, inner shaft 320 is illustrated as having a smaller ID than the ID of elongated shaft 302. In addition to functioning as an interference part, the ID of inner shaft 320 may more effectively accommodate a reduction in OD of the elongated catheter sheath 404. Referring again to FIG. 10, the ID of neck portion 332 may also more effectively accommodate a reduction in OD of the elongated catheter sheath 404 in addition to functioning as an interference part. Thus, a minimum clearance between the ID of inner shaft 320 or ID of neck portion 332 and the OD of the elongated catheter shaft 404 may provide enhanced resistance to fluid-spray back.

Figure 11A:
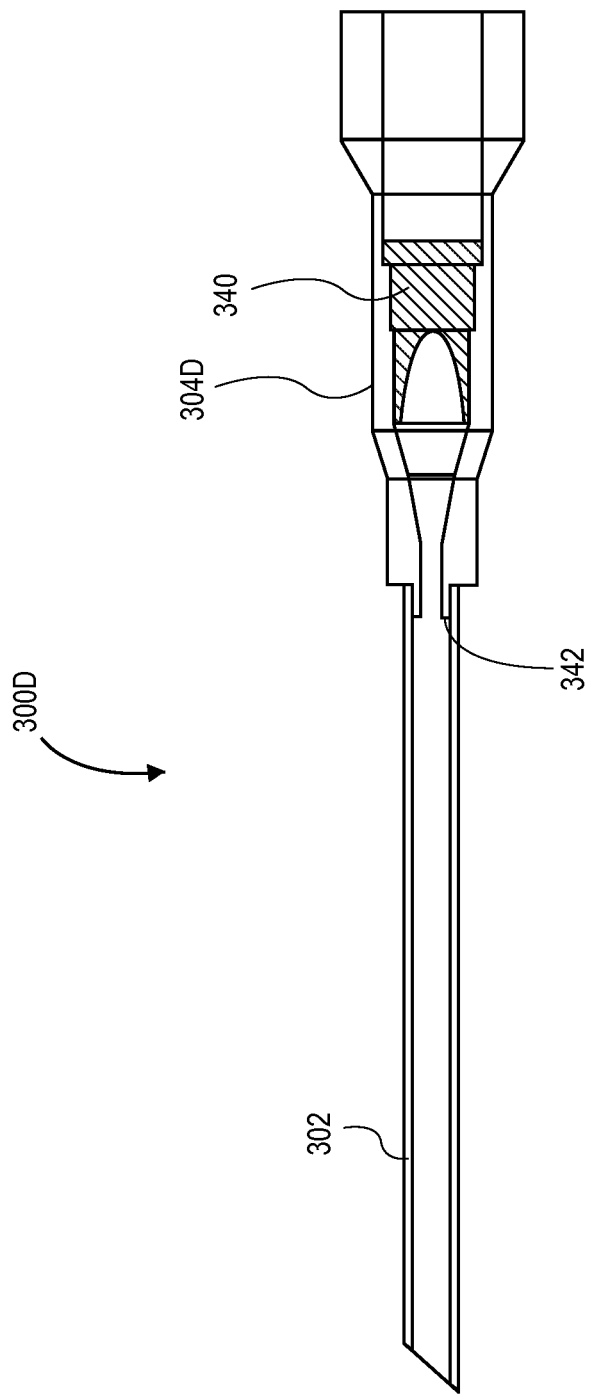
FIGS. 11A-11C are cross-sectional side view illustrations of tip protector sleeves incorporating various sealing valves in accordance with embodiments of the invention.
Figure 11B:
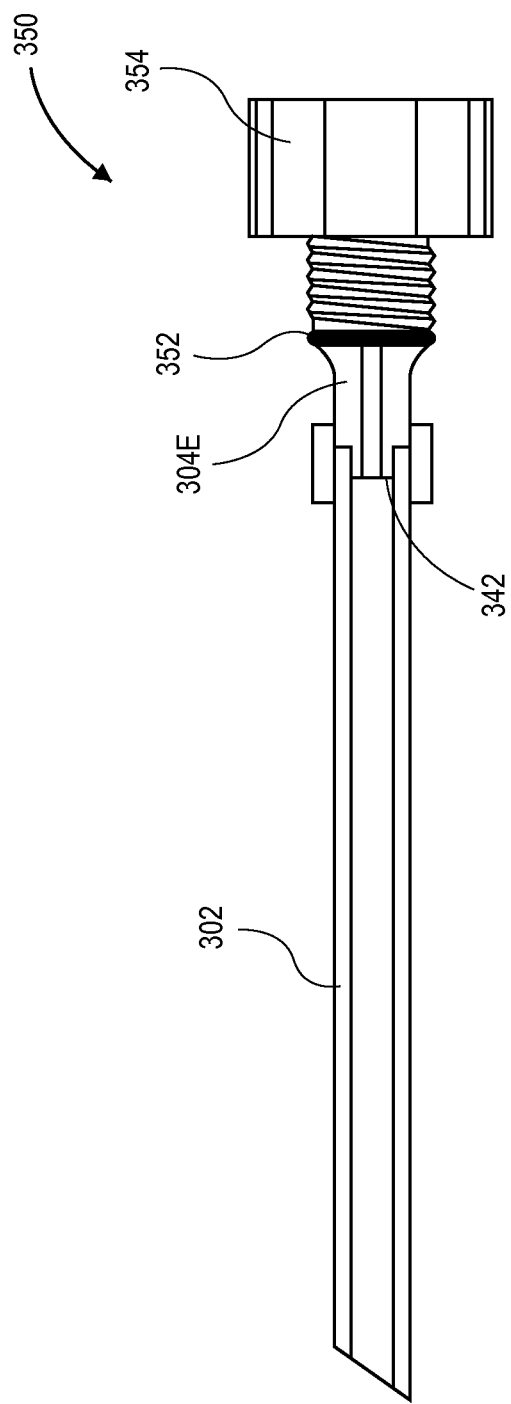
Figure 11C:
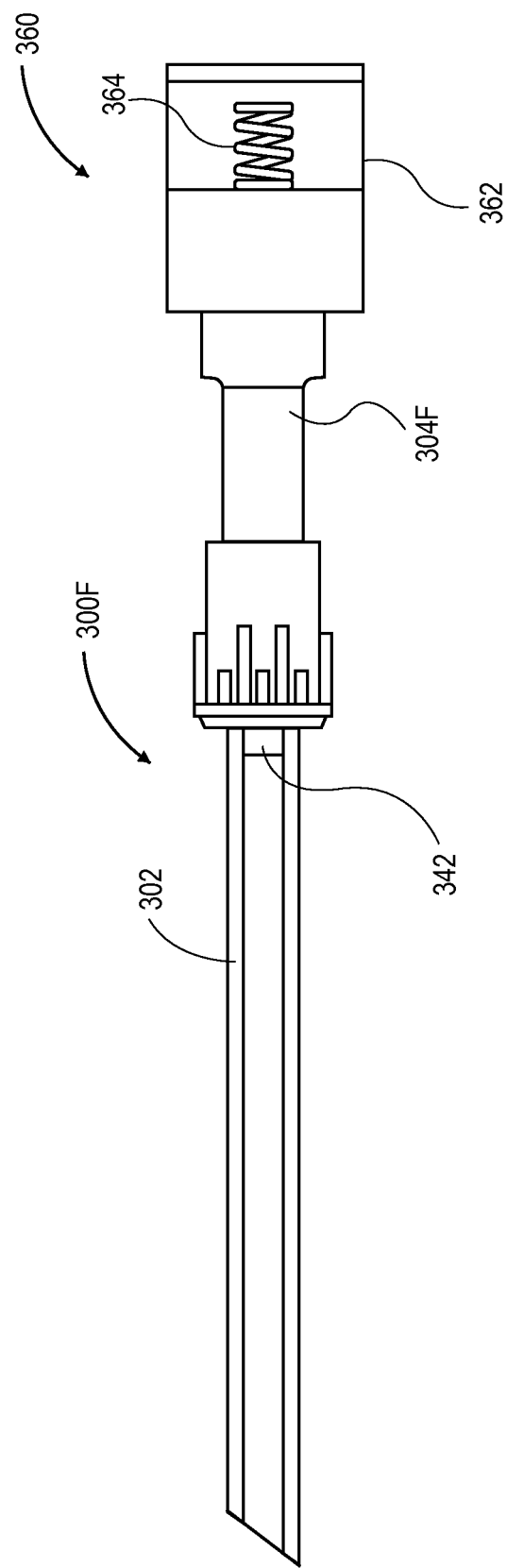

FIGS. 11A-11C are illustrations embodiments of a tip protector sleeve incorporating various sealing valves to reduce the amount of fluid spray-back and leakage between the tip protector sleeve and elongated sheath of the delivery catheter assembly. While illustrated separately, it is understood that the embodiments illustrated in FIGS. 11A-11C may be combined with other embodiments of the invention. More specifically, any of the sealing valves described in reference to the illustrations in FIGS. 11A-11C may be combined with any of the embodiments further describing the proximal-stop and distal-stop positions.

FIG. 11A is an illustration of a tip protector sleeve 300D including an elongated shaft 302, a housing 304D, and valve 340. Housing 304D may function as a stop mechanism that controls the insertion depth of the tip protector sleeve 300D into the working channel and may perform the function as a handle for gripping by the operator. The elongated shaft 302 may be coupled to a distal tip 342 of the housing 304D which may function as a backstop for interference with a bump 408 fixed to the elongated catheter sheath 404 at the distal-stop position. Housing 304D additionally houses valve 340 which is capable of accommodating multiple variations in OD of the elongated catheter sheath 404. For example, valve 340 may be a silicone valve containing a slit at the distal end that allows for a catheter shaft to pass through it. The silicone material may allow for the slit to conform to different shapes or diameters while providing a seal. Due to the geometry on the distal end of the silicone valve, as fluid tries to pass from distal to proximal, the end of the valve may be pushed closed due to a chamfer on the end of the valve.

FIG. 11B is an illustration of a tip protector sleeve 300E including an elongated shaft 302, a housing 304E, and a compression valve 350 including an screw cap 354 which may be threaded down onto an O-ring 352 to compress it against the elongated catheter sheath 404. Housing 304E may function as a stop mechanism that controls the insertion depth of the tip protector sleeve 300E into the working channel and may perform the function as a handle for gripping by the operator. The elongated shaft 302 may be coupled to a distal tip 342 of the housing 304E which may function as a backstop for interference with a bump fixed to the elongated catheter sheath at the distal-stop position.

FIG. 11C is an illustration of a tip protector sleeve 300F including an elongated shaft 302, a housing 304F, and a compression valve 360 including a cap 362, a compression spring 364 and a thin walled tube (not illustrated) inside the housing. For example, the thin walled tube may be made of a material such as silicone. Threads between the cap 362 and the housing 304F apply a twist motion to the tube. When the tube is twisted, an inner diameter of the tube tightens like an iris. The compression spring 364 keeps the cap 362 extended and the threads hold the twist or keep the iris closed. When the cap 362 is pushed towards the housing 304F (spring compressed) the cap 362 untwists and the iris opens. In this manner the opening of the iris can be adjusted based upon the OD of the elongated catheter sheath 404. Similar to tip protector sleeves 300D and 300E, housing 304F may function as a stop mechanism that controls the insertion depth of the tip protector sleeve 300F into the working channel and may perform the function as a handle for gripping by the operator. The elongated shaft 302 may be coupled to a distal tip 342 of the housing 304F which may function as a backstop for interference with a bump fixed to the elongated catheter sheath at the distal-stop position.

A delivery catheter assembly in accordance with embodiments of the invention may be utilized to deliver an insert to an ovarian pathway (e.g. a fallopian tube) of a female body. The delivery catheter assembly may protect the tip of an elongated catheter sheath, guidewire, or insert during piercing of a sealing cap and insertion into the working channel and past a valve clamp of a hysteroscope system and reduce the amount of fluid spray-back and leakage associated with inserting a delivery catheter assembly into the working channel of a hysteroscope system. In an embodiment, the delivery catheter assembly includes a control device, an elongated catheter sheath having a distal end and a proximal end connected to the control device, and a tip protector sleeve locked onto the elongated catheter sheath and slideable over a length of the elongated catheter sheath between a proximal-stop position and a distal-stop position along the elongated catheter sheath. The delivery catheter assembly may further include an insert releasably disposed within the elongated catheter sheath. In an embodiment, the insert extends distally beyond the elongated catheter sheath. In an embodiment, the insert includes a preformed bend, as illustrated in FIG. 5, which may be utilized to assist with navigation through a curved portion of a fallopian tube. Upon providing the delivery catheter assembly the operator may grasp a flanged mechanical stop 304 or other suitable portion of the tip protector sleeve 300 to position the tip protector sleeve at the distal-stop position illustrated in FIG. 6. If a sealing valve is present on the tip protection sleeve 300, the sealing valve may then be tightened onto the elongated catheter sheath 404 if necessary to provide an optimal seal to protect against fluid spray-back and leakage.

Figure 12B:
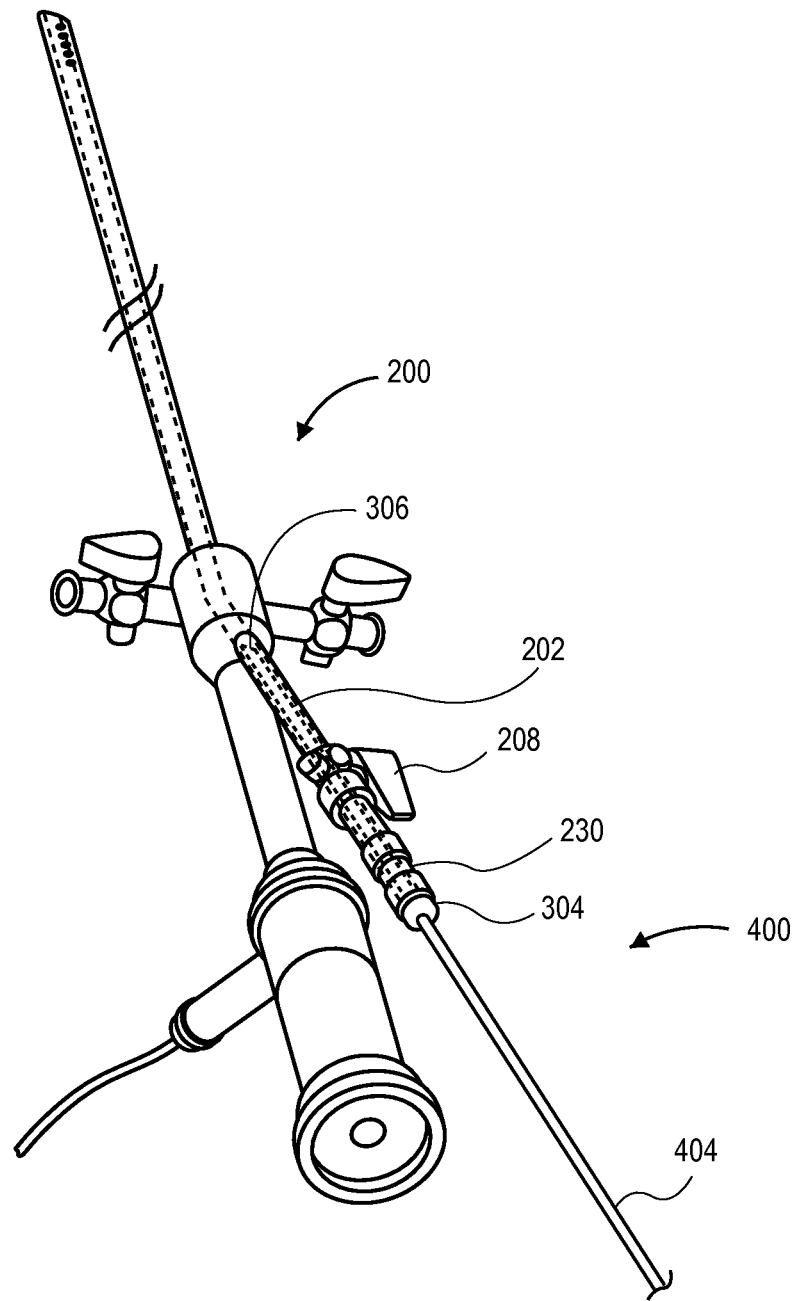
Figure 12C:
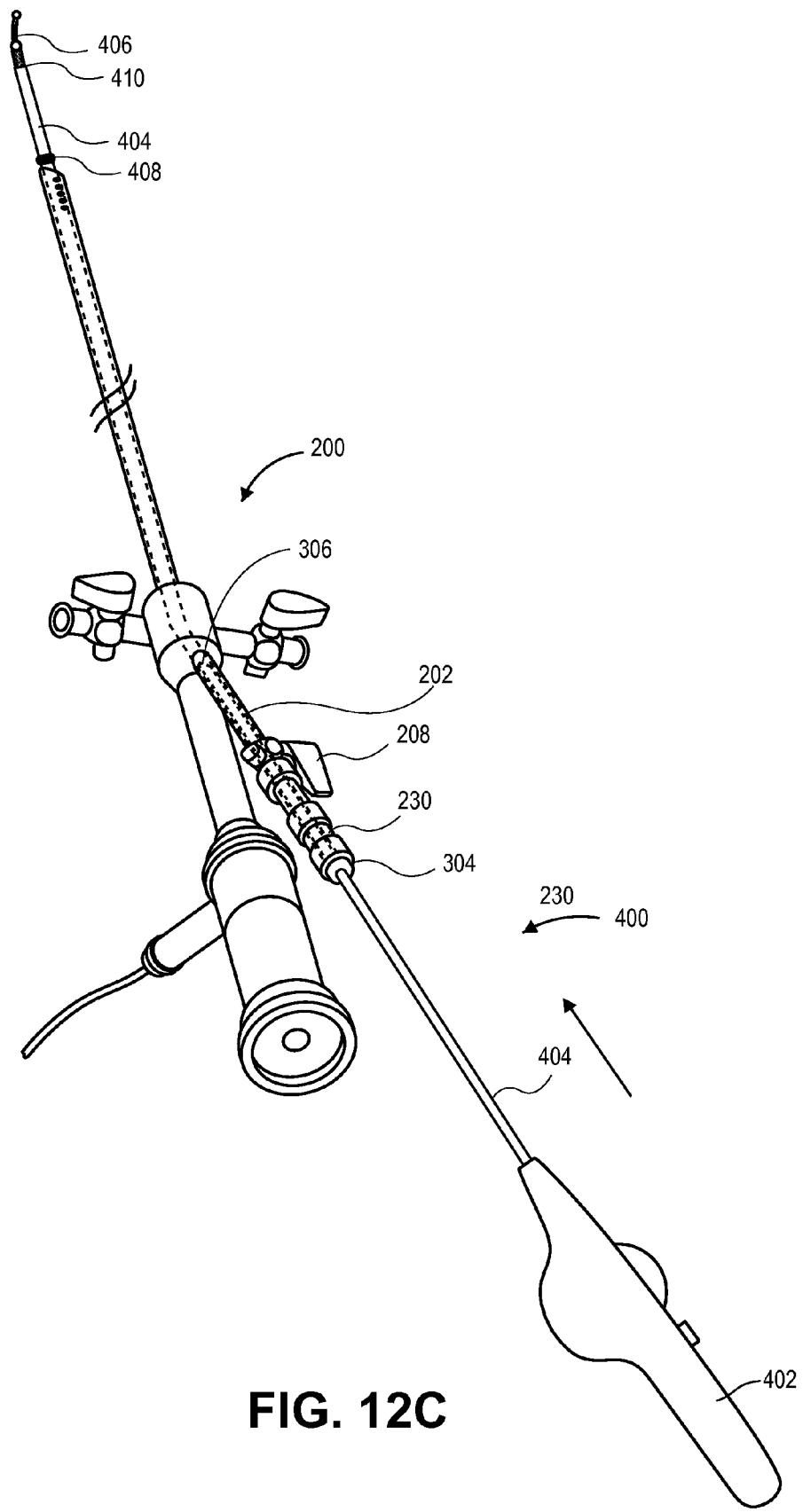

Referring now to FIGS. 12A-12C, the operator may then pierce a pierceable end 232 of a sealing cap 230 with the tip protector sleeve 300 and insert the tip protector sleeve 300 through an access port 206 of a hysteroscope system 200 and into the working channel 202 of the hysteroscope system. During insertion the tip protector sleeve 300 may be advanced past a valve clamp 208 of the hystero scope system. The tip protector sleeve protects against the possibility of the exposed portion of the insert 406 from catching on the valve clamp 208 and compromising the insert integrity. In accordance with embodiments of the invention, the distal end 410 of the elongated catheter sheath 404 and insert 406 are inserted through the sealing cap 230 and access port 206, and into the working channel 202 of the hysteroscope system simultaneously with the tip protector sleeve 300 in the distal-stop position. The simultaneous insertion of the tip protector sleeve 300 and elongated catheter sheath 404 may avoid a problem of fluid spray-back associated with sequentially inserting an introducer followed by an elongated catheter sheath. In an embodiment, the tip protector sleeve 300 may be advanced into the working channel simultaneously with the elongated catheter sheath and insert 406 until the flanged mechanical stop 304 abuts against the access port 206 or sealing cap 230, if present, as illustrated in FIG. 12B.

The distal end 410 of the elongated catheter sheath 404 may then be advanced past the hysteroscope system 200 as illustrated in FIG. 12C, and onto a target location with the body lumen. The insert 406 may then be deployed into the body lumen. Depending upon operator preference, the tip protector sleeve 300 may remain inserted in the working channel 202 during the elongated catheter sheath 404 advancement and insert 406 deployment procedures or removed from the working channel 202. In accordance with many embodiments of the invention it is understood that the tip protector sleeve 300 is permanently locked onto the elongated catheter sheath. It is also contemplated that the tip protector sleeve 300 could be removed from the catheter assembly after initially advancing the catheter assembly into the working channel, for example, by including a tear joint in the tip protector sleeve in which the tip protector sleeve can be manually torn off of the elongated catheter sheath by the operator.

In an embodiment, the insert 406 and distal end 410 of the elongated catheter sheath 404 are advanced to the target location within the body lumen while the flanged mechanical stop 304 on the tip protector sleeve 300 abuts the access port 206 or sealing cap 320, if present. The amount of elongated catheter sheath 404 spanning between the flanged mechanical stop 304 and control device 402 may depend upon the procedure and patient's anatomy. It is envisioned that circumstances arise where the operator may wish to insert the entire available working length of the elongated catheter sheath 404 into the patient and advance the control device 402 all the way to the access port or sealing cap, if present. In accordance with embodiments of the invention illustrated in FIGS. 5B-5D, this can be possible by including a cavity 420 in the control device 402 to accommodate the flanged mechanical stop 304.

Once the insert 406 is deployed into the body lumen the delivery catheter assembly may be withdrawn from the working channel of the hysteroscope system. In one embodiment, during withdrawal of the delivery catheter assembly 400 from the working channel, the bump 408 on the elongated catheter sheath 404 may be withdrawn proximally against the backstop of the tip protector sleeve 300 and cause the tip protector sleeve 300 to be withdrawn from the working channel 202 of the hysteroscope system 200. In another embodiment, the flanged mechanical stop 304 on the tip protector sleeve 300 can be fastened to the control device 402. In this manner, during withdrawal of the delivery catheter assembly 400 from the working channel, the tip protector sleeve 300 remains fastened to the control device 402.

In the foregoing specification, various embodiments of the invention have been described. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Hence, the scope of the present invention is limited solely by the following claims.

What is claimed is:

1. A delivery catheter assembly comprising:
   a control device;
   an elongated catheter sheath having a distal end and a proximal end connected to the control device;
   a tip protector sleeve locked onto the elongated catheter sheath and slideable over a length of the elongated catheter sheath between a proximal-stop position and a distal-stop position along the elongated catheter sheath while locked onto the elongated catheter sheath; and
   an interference stop comprising a male interference part fixed to the elongated catheter sheath at a first distance from the distal end of the elongated sheath, and a female interference part;
   wherein the male interference part interferes with sliding of the female interference part over the elongated sheath such that the interference stop determines the distal-stop position and prevents the tip protector sleeve from sliding off of the distal end of the elongated catheter sheath, and the tip protector sleeve is longer than the first distance such that the tip protector sleeve extends distally beyond the distal end of the elongated catheter sheath when at the distal-stop position.

2. The delivery catheter assembly of claim 1, wherein the tip protector sleeve comprises an elongated shaft and a backstop together functioning as the female interference part.

3. The delivery catheter assembly of claim 2, wherein the male interference part comprises a bump fixed to the elongated catheter sheath.

4. The delivery catheter assembly of claim 3, wherein the bump comprises a band fixed to and encircling the elongated catheter sheath.

5. The delivery catheter assembly of claim 4, wherein a distal end of the band is crimped onto the elongated catheter sheath, and a proximal end of the band is not crimped onto the elongated shaft.

6. The delivery catheter assembly of claim 2, wherein the backstop has an inside diameter which is smaller than an outside diameter of the male interference part.

7. The delivery catheter assembly of claim 6, further comprising a molded bead fixed to a proximal end of the elongated shaft.

8. The delivery catheter of claim 7, wherein the molded bead comprises:
   a distal portion surrounding the proximal end of the elongated shaft;
   a shoulder portion extending proximally of the elongated shaft; and
   the backstop, wherein the backstop abuts the proximal end of the elongated shaft.

9. The delivery catheter assembly of claim 6, wherein the tip protector sleeve further comprises an inner shaft fixed to a proximal end of the elongated shaft, and the backstop is a distal end of the inner shaft.

10. The delivery catheter assembly of claim 1, further comprising an insert disposed within and extending distally beyond the distal end of the elongated catheter sheath, wherein the tip protector sleeve extends distally beyond the insert when at the distal-stop position.

11. The delivery catheter assembly of claim 1, wherein the tip protector sleeve further comprises a sealing valve.

\* \* \* \* \*